United States Patent [19]

Bauer et al.

[11] Patent Number: 4,994,614

[45] Date of Patent: Feb. 19, 1991

[54] AMINE OXIDE PROCESS

[75] Inventors: Dennis P. Bauer; Teresa K. Summerford, both of Baton Rouge, La.

[73] Assignee: Ethyl Corporation, Richmond, Va.

[21] Appl. No.: 138,208

[22] Filed: Dec. 28, 1987

Related U.S. Application Data

[63] Continuation-in-part of Ser. No. 132,805, Dec. 14, 1987, abandoned.

[51] Int. Cl.$^5$ .................. C07C 239/00; C07C 259/00
[52] U.S. Cl. ...................................... 564/300; 564/301
[58] Field of Search ................................ 564/300, 301

[56] References Cited

U.S. PATENT DOCUMENTS

| | | | |
|---|---|---|---|
| 3,655,764 | 2/1969 | Bader et al. | 564/301 |
| 3,960,954 | 6/1976 | Russell et al. | 564/267 |
| 4,247,480 | 1/1981 | Murata et al. | 564/298 |
| 4,649,221 | 3/1987 | Ravichandran et al. | 564/300 |
| 4,681,756 | 7/1987 | Mergens et al. | 424/451 |

FOREIGN PATENT DOCUMENTS 5683465  3/1979  Japan .

OTHER PUBLICATIONS

Kabacoff et al., ACS Symposium Series No. 174, "N-Nitro Compounds", pp. 149-156.

*Primary Examiner*—Nathan M. Nutter
*Attorney, Agent, or Firm*—Joseph D. Odenweller; Patricia J. Hogan

[57] ABSTRACT

Tert-amine oxides that are substantially free of nitrosamines are made by reacting a tert-amine, e.g., dodecyl dimethylamine, with aqueous hydrogen peroxide in the presence of the synergistic combination of (a) ascorbic acid and (b) a promoter formed from carbon dioxide.

22 Claims, No Drawings

1

AMINE OXIDE PROCESS

BACKGROUND OF THE INVENTION

This application is a continuation-in-part of U.S. Pat. application Ser. No. 132,805 filed Dec. 14, 1987 and now abandoned.

Tertiary amine oxides are conventionally made by the reaction of an appropriate tert-amine with aqueous hydrogen peroxide. The reaction is generally conducted at 50°–75° C. and requires a long reaction period to obtain complete conversion of the amine. Several promoters for the reaction have been reported. Among the more effective is carbon dioxide. Murato et al. U.S. Pat. No. 4,247,480 report the reaction of N,N-diethyl 3,7-dimethyl-2,6-octadienylamine with 30 percent aqueous hydrogen peroxide at 55°–65° C. in the presence of carbon dioxide to give a 99 percent yield of the corresponding amine oxide. Also Japan Pat. application No. 56-83465 describes the use of ascorbic acid to stabilize shampoo and detergent compositions which contain an amine oxide from degradation leading to color formation and foul odor during storage.

Nitrosamines are formed as minor by-products in the conventional preparation of tert-amine oxides using aqueous hydrogen peroxide. Although the amount of nitrosamine is very small, on the order of parts per billion (ppb), this small amount renders the amine oxide unsuitable in many applications that involve human contact. This is because nitrosamines are reported to be carsinogenic and/or mutagenic. Amine oxides have properties that would make them very useful in shampoo, hair conditioners, dish and laundry detergent, fabric softeners and the like. Hence a need exists for a method for making tert-amine oxides in high conversion and yield and at a fast reaction rate and at the same time producing a tert-amine oxide product that is substantially free of nitrosamines. The present invention provides such a process.

SUMMARY

It has now been discovered that tert-amine oxides that are substantially free from nitrosamines can be produced in high yield at a fast reaction rate by reacting a tert-amine with aqueous hydrogen peroxide in the presence of ascorbic acid and a promoter formed from carbon dioxide. This is quite unexpected because under the same reaction conditions, amine oxides made in the presence of either carbon dioxide or ascorbic acid individually contained significant quantities of nitrosamines.

DESCRIPTION OF THE PREFERRED EMBODIMENTS

A preferred embodiment of the invention is a process for making a substantially nitrosamine-free amine oxide by reacting a tert-amine capable of forming an amine oxide with aqueous hydrogen peroxide in the presence of the synergistic combination of (a) ascorbic acid and (b) a promoter formed by adding carbon dioxide to the reaction mixture.

The process is applicable to any tert-amine capable of forming an amine oxide. These are well known to organic chemists. They include amines which do not have a hydrogen atom bonded to the amine nitrogen atom. Such amines include trialkylamines; triarylamines; triarylalkylamines; mixed alkyl-aryl, alkyl-arylalkyl, aryl-arylalkyl or alkyl-aryl-arylalkylamines; tricycloalkylamines; alkyl-cycloalkylamines; aryl-cycloalkylamines; cyclic amines, e.g. N-methyl piperidine, N,N'-dimethyl piperazine, pyridine, 2-methyl pyridine, N-methyl pyrrolidine, N-methyl pyrrolidone, N-ethyl morpholine and the like.

In a more preferred embodiment the tert-amine has the formula $R^1R^2R^3N$ wherein $R^1$ is an alkyl group containing 1–30 carbon atoms and $R^2$ and $R^3$ are alkyl groups containing 1–30 carbon atoms, cycloalkyl groups containing 5–12 carbon atoms, aryl groups containing 6–12 carbon atoms, aralkyl groups containing 7–12 carbon atoms or any two of the R groups can join to form a carbocyclic or hetrocyclic ring or all three of the R groups may participate to form a pyridine ring.

The process is applicable to any of a broad range of tert-amines such as butyldimethylamine, hexyl dimethylamine, isobutyl dimethylamine, 2-ethylhexyl dimethylamine, octyl dimethylamine, decyl dimethylamine, dodecyl dimethylamine, tetradecyl dimethylamine, hexadecyl dimethylamine, eicosyl dimethylamine, docosyl dimethylamine, triacontyl dimethylamine, tributylamine, butyl diethylamine, isobutyl diethylamine, decyl butyl ethylamine, hexadecyl hexyl methylamine, eicosyl dibutylamine, trioctylamine, tridodecylamine, dieicosyl ethylamine, ditriacontyl methylamine, N,N,-dimethylaniline, N-methyl-N-dodecylaniline, cyclopentyl dimethylamine, cyclohexyl dimethylamine, dicyclohexyl methylamine, cyclododecyl dimethylamine, diphenyl butylamine, p-tolyl diethylamine, α-naphthyl-butylmethylamine, benzyl butyl methylamine, α-methylbenzyl butyl methylamine, 4-butylbenzyl octyl methylamine, dibenzyl butylamine, 4-pentyl-benzyl dibutylamine, N-methylmorpholine, N-methylmorpholine, N-butylmorpholine, N-methylpiperidine, N-dodecylpiperidine, N-octadecylpiperidine, N-triacontylpiperidine, N-methylpiperazine, N-butylpiperazine, N-octylpiperazine, N-phenylpiperidine, N-benzylpiperidine, N-cyclohexylpiperidine, pyridine and the like.

In a more preferred embodiment the tert-amine is a primary trialkylamine having the structure $R^1R^2R^3N$ wherein $R^1$, $R^2$ and $R^3$ are primary alkyls having 1–30 carbon atoms. Representative examples of these include but are not limited to trimethylamine, tri-n-pentylamine, tri-n-dodecylamine, n-octadecyl di-(n-butyl)amine, n-eicosyl di-(n-decyl)amine, n-triacontyl, n-dodecyl methylamine and the like.

In a still more preferred embodiment $R^1$ is a primary alkyl group containing 6–22 carbon atoms and $R^2$ and $R^3$ are independently selected from methyl and ethyl groups.

In a further preferred embodiment $R^1$ is a mainly linear primary alkyl containing 8–20 carbon atoms and $R^2$ and $R^3$ are methyl groups. By "mainly linear" is meant that over 50 percent, more preferably 70 percent and most preferably 90 percent of the $R^1$ groups are linear alkyls containing 8–20 carbon atoms.

Examples of these preferred embodiments are octyl dimethylamine, decyl dimethylamine, dodecyl dimethylamine, tetradecyl dimethylamine, hexadecyl dimethylamine, octadecyl dimethylamine, eicosyl dimethylamine and mixtures thereof.

In another more preferred embodiment of the invention, both $R^1$ and $R^2$ are independently selected from primary alkyls containing 6–22 carbon atoms and $R^3$ is a methyl or ethyl group.

In a highly preferred embodiment $R^1$ and $R^2$ are independently selected from mainly linear primary alkyl groups containing 8–20 carbon atoms and $R^3$ is methyl. Examples of this highly preferred embodiment are dioctyl methylamine, didecyl methylamine, didodecyl methylamine, ditetradecyl methylamine, dihexadecyl methylamine, dioctadecyl methylamine, dieicosyl methylamine, decyl octyl methylamine, dodecyl octyl methylamine, tetradecyl decyl methylamine, hexadecyl tetradecyl methylamine, octadecyl hexadecyl methylamine, eicosyl dodecyl methylamine and the like including mixtures thereof.

Any aqueous hydrogen peroxide can be used including those containing 3–100 percent $H_2O_2$. Preferably the hydrogen peroxide is 20–70 weight percent active $H_2O_2$. When the tertamine is linear $C_{8-20}$ alkyl dimethylamine, it is preferred that the aqueous hydrogen peroxide be about 20–40 weight percent $H_2O_2$ to avoid gel formation. Alternatively, more concentrated hydrogen peroxide can be used and additional water co-fed to maintain a stirrable reaction mixture. Likewise, co-solvents such as lower alcohol, e.g., isopropanol, isobutanol and the like, can be used to avoid gelation.

The amount of hydrogen peroxide should be at least a stoichiometric amount. A useful range is about 1–5 moles of $H_2O_2$ and more preferably 1–1.5 mole of $H_2O_2$ per mole of tert-amine. A highly preferred amount is about 1.05–1.3 moles of $H_2O_2$ and especially about 1.1–1.2 moles of $H_2O_2$ per mole of tert-amine. Any excess $H_2O_2$ remaining after the reaction can be destroyed by the addition of a reducing agent or a peroxide decomposition catalyst such as manganese dioxide.

When the process is conducted using a di-linear alkyl methylamine, the process can be carried out using more concentrated aqueous hydrogen peroxide such as about 45–70 weight percent hydrogen peroxide. When the di-linear alkyls contain up to about 6–12 carbon atoms each, the reaction mixture will remain substantially gel free. When the di-linear alkyls contain 14 or more carbon atoms the reaction mixture will set up to a dry flakeable solid on cooling.

The reaction can be conducted over a wide temperature range. The temperature should be high enough to cause the reaction to proceed at a reasonable rate but not so high as to lead to decomposition of the reactants or products. A useful temperature range is from about 0°–100° C. A more preferred temperature range is about 30°–90° C. A still more preferred temperature range is about 40°–75° C. Most preferably the reaction is conducted at about 50°–75° C. In this temperature range the reaction is quite rapid and normally, without the presence of both carbon dioxide and ascorbic acid, would produce significant quantities of nitrosamines. Excellent results have been achieved at about 65° C.

The amount of carbon dioxide can vary over a wide range. It is required that the amount of carbon dioxide in the reaction mixture in whatever form it exists be an amount which causes the reaction to proceed at a faster rate than the rate achieved without the addition of carbon dioxide. In other words there should be at least a promoter amount of carbon dioxide. The upper limit of carbon dioxide is not critical and is determined by the solubility limit of carbon dioxide in the reaction mixture. A useful concentration is about 0.05–5.0 weight percent based on the weight of the initial tert-amine. Even more carbon dioxide can be used, e.g. 10 weight percent or more but this generally requires the reaction to be conducted under carbon dioxide pressure. A useful pressure range when carbon dioxide pressure is used is about 1–500 psig and preferably about 5–100 psig and more preferably about 10–50 psig.

Another way to add the carbon dioxide is to dissolve the carbon dioxide in the tert-amine prior to adding the amine to the reaction vessel. In another mode of operation the carbon dioxide can be dissolved in the aqueous hydrogen peroxide prior to adding the aqueous hydrogen peroxide to the reaction vessel. Alternatively, the carbon dioxide can be dissolved in any water or other solvent (e.g. alcohol) added to the reaction vessel. Carbon dioxide is fairly reactive and will form other species when added to the reaction system. For example carbon dioxide dissolves in water to form carbonic acid which in this reaction is considered the equivalent of carbon dioxide. Likewise carbon dioxide may react with the tert-amine to form other catalytic species which in the present process are considered the equivalent of carbon dioxide.

The amount of ascorbic acid should be an amount which when used in combination with the carbon dioxide promoter yields a tert-amine oxide that is substantially free of nitrosamines. In other words, it should be a nitrosamine inhibiting amount. A useful concentration of ascorbic acid is about 0.005–10 weight percent based on the tert-amine reactant. A preferred concentration of ascorbic acid is about 0.05–5 weight percent. A more preferred concentration is about 0.1–2 weight percent and a most preferred concentration of ascorbic acid is 0.2–1 weight percent.

Instead of ascorbic acid, salts of ascorbic acid can be used such as ammonium or alkaline metal salts. Likewise isomeric forms of ascorbic acid are included in the scope of the invention.

A series of reactions was conducted which revealed the synergistic effect of the combination of carbon dioxide and ascorbic acid. The following examples describe this series of experiments.

EXAMPLE 1

Reaction with Carbon Dioxide Promoter Only

In a reaction vessel was placed 250 grams of dodecyl dimethylamine. The vapor space above the liquid was purged with carbon dioxide and a carbon dioxide sweep through the vapor space was continued during the reaction permitting carbon dioxide absorption up to its solubility limit in the liquid phase. While stirring at 65° C., 86 grams of 50 weight percent aqueous hydrogen peroxide and 584 ml water which was sufficient to maintain a fluid reaction mixture and give a final amine oxide concentration of about 30 weight percent, were concurrently added over a 30 minute period. Stirring was continued for 150 minutes at 65° C. The reaction mixture was cooled to room temperature and analyzed, by spectroscopic and wet chemical methods, as follows:

| | |
|---|---|
| dodecyl dimethylamine oxide | 30 percent |
| dodecyl dimethylamine | 0.2 percent |

EXAMPLE 2

Reaction with Ascorbic Acid Inhibitor Only

This experiment was conducted in the same manner as Example 1 except that the carbon dioxide purge (and sweep) was replaced with a nitrogen pad and 0.5 weight percent ascorbic acid, based on the tert-amine, was added at the start of the reaction. After the concurrent addition of 84 g of hydrogen peroxide and 584 ml water over 0.5 hour, the reaction mixture was stirred for an additional 10 hours. The reaction mixture analyzed as follows:

| | |
|---|---|
| dodecyl dimethylamine oxide | 29 percent |
| dodecyl dimethylamine | 0.5 percent |

EXAMPLE 3

The Synergistic Combination

This experiment was conducted in the same manner as Example 1 including the carbon dioxide purge and sweep. In addition, 0.5 weight percent ascorbic acid was added at the start of the reaction followed by the concurrent addition of 84 g of hydrogen peroxide and 584 ml water. The final reaction mixture analyzed as follows:

| | |
|---|---|
| dodecyl dimethylamine oxide | 30 percent |
| dodecyl dimethylamine | 0.02 percent |

Each reaction mixture from Examples 1, 2 and 3 was analyzed for nitrosamines using a Thermal Energy Analyzer by an adaptation of the method described in Krull, I.S., et al., Anal. Chem 51, 1706 (1979). The nitrosamine results obtained were as follows:

| | Example | | |
|---|---|---|---|
| | 1 | 2 | 3 |
| N,N-dimethylnitrosamine | 96 ppb | 37 ppb | N.D. [1] |
| N-methyl-N-dodecyl nitrosamine | N.D. | 216 ppb | N.D. |

[1] Not detected. The limits of detection by this method are N,N-dimethyl nitrosamine 10 ppb and N-methyl-N-dodecyl nitrosamine 80 ppb.

The above results show that the use of carbon dioxide alone (Example 1) does not eliminate the formation of nitrosamines under the above reaction conditions. Likewise the experiments show that ascorbic acid alone (Example 2) leads to the formation of substantial quantities of nitrosamines. Surprisingly, it was discovered that the combination of carbon dioxide and ascorbic acid (Example 3) reduced the amount of nitrosamines below the limit of detection.

What is claimed is:

1. A process for making a substantially nitrosamine-free tert-amine oxide, said process comprising reacting at a temperature in the range of about 30°–90° C. a tert-amine capable of forming a tert-amine oxide with at least a stoichiometric amount of about 20–70 weight percent active aqueous hydrogen peroxide in the presence of the synergistic combination of (a) an effective amount within the range of about 0.005–10 weight percent of ascorbic acid or salt thereof and (b) a promotor formed by adding about 0.05–5 weight percent, based on the weight of the initial tert-amine, of carbon dioxide to the reaction mixture.

2. A process of claim 1 wherein the reaction is conducted in the presence of a synergistic combination of ascorbic acid and the promotor.

3. A process of claim 2 wherein said tert-amine is a trialkylamine.

4. A process of claim 3 wherein said trialkylamine is a $C_{6-22}$ alkyl di-$C_{1-2}$ alkylamine.

5. A process of claim 4 wherein said trialkylamine is octyl dimethylamine.

6. A process of claim 4 wherein said trialkylamine is decyl dimethylamine.

7. A process of claim 4 wherein said trialkylamine is dodecyl dimethylamine.

8. A process of claim 4 wherein said trialkylamine is tetradecyl dimethylamine.

9. A process of claim 4 wherein said trialkylamine is hexadecyl dimethylamine.

10. A process of claim 4 wherein said trialkylamine is octadecyl dimethylamine.

11. A process of claim 3 wherein said trialkylamine is a di-$C_{6-22}$ alkyl $C_{1-2}$ alkylamine.

12. A process of claim 11 wherein said trialkylamine is dioctyl methylamine.

13. A process of claim 11 wherein said trialkylamine is didecyl methylamine.

14. A process of claim 11 wherein said trialkylamine is didodecyl methylamine.

15. A process of claim 2 conducted at 50°–75° C.

16. A process of claim 15 wherein said tert-amine is a $C_{6-22}$ alkyl dimethylamine.

17. A process of claim 16 wherein said tert-amine is decyl dimethylamine.

18. A process of claim 16 wherein said tert-amine is dodecyl dimethylamine.

19. A process of claim 15 wherein said tert-amine is a di-$C_{6-22}$ alkyl methylamine.

20. A process of claim 19 wherein said tert-amine is dioctyl methylamine.

21. A process of claim 19 wherein said tert-amine is didecyl methylamine.

22. A process of claim 19 wherein said tert-amine is didodecyl methylamine.

* * * * *